United States Patent
Jutras et al.

(10) Patent No.: US 7,107,091 B2
(45) Date of Patent: Sep. 12, 2006

(54) MULTIPLE BONE TRACKING

(75) Inventors: Sébastien Jutras, Montreal (CA); Dominic Picard, Verdun (CA); Pierre Couture, Montreal (CA); François Poulin, Montreal (CA); Louis-Philippe Amiot, Hampstead (CA); James Anglehart, Montreal (CA)

(73) Assignee: Orthosoft Inc., Montréal (CA)

( * ) Notice: Subject to any disclaimer, the term of this patent is extended or adjusted under 35 U.S.C. 154(b) by 595 days.

(21) Appl. No.: 10/202,609

(22) Filed: Jul. 25, 2002

(65) Prior Publication Data

US 2004/0019263 A1 Jan. 29, 2004

(51) Int. Cl.
*A61B 5/05* (2006.01)
*A61B 19/00* (2006.01)

(52) U.S. Cl. .................. 600/429; 600/130; 600/429

(58) Field of Classification Search .......... 600/429, 600/417, 425, 426, 427, 428, 130; 623/16.11, 623/17.11; 606/130, 1
See application file for complete search history.

(56) References Cited

U.S. PATENT DOCUMENTS

| | | | | |
|---|---|---|---|---|
| 4,457,311 A | * | 7/1984 | Sorenson et al. | 600/447 |
| 4,723,544 A | * | 2/1988 | Moore et al. | 606/130 |
| 5,080,662 A | * | 1/1992 | Paul | 606/130 |
| 5,474,555 A | | 12/1995 | Puno et al. | |
| 5,899,901 A | | 5/1999 | Middleton | |
| 6,006,126 A | | 12/1999 | Cosman | |
| 6,226,548 B1 | | 5/2001 | Foley et al. | |
| 6,236,875 B1 | | 5/2001 | Bucholz et al. | |
| 6,241,735 B1 | | 6/2001 | Marmulla | |
| 6,340,363 B1 | | 1/2002 | Bolger et al. | |
| 6,678,545 B1 | * | 1/2004 | Bucholz | 600/426 |
| 6,684,098 B1 | * | 1/2004 | Oshio et al. | 600/429 |
| 6,749,614 B1 | * | 6/2004 | Teitelbaum et al. | 606/61 |
| 6,821,277 B1 | * | 11/2004 | Teitelbaum | 606/61 |

* cited by examiner

*Primary Examiner*—Daniel Robinson
(74) *Attorney, Agent, or Firm*—Ogilvy Renault LLP (57) ABSTRACT

A surgical device adapted for use with an image guided surgical system to facilitate monitoring inter-dependently mobile bone elements. A rigidly connected multiple-point anchor assembly is releasably engageable to at least two inter-dependently mobile bone elements and immobilizes the bone elements such that no relative movement therebetween is possible, and a complex rigid body comprising the immobilized bone elements and the multiple-point anchor assembly is formed. A trackable member is fastened to the multiple-point anchor assembly and comprises a detectable element adapted to be located and tracked in three dimensional space by the image guided surgical system, thereby defining position and movement of the complex rigid body.

27 Claims, 5 Drawing Sheets

MULTIPLE BONE TRACKING

FIELD OF THE INVENTION

The present invention relates generally to an apparatus and method for multi-bone tracking, and more particularly to a trackable multi-vertebrae clamp for use with a computer assisted surgical system, and particularly for pedicle screw placement.

BACKGROUND OF THE INVENTION

Increasingly common spinal surgical procedures, such as those performed to treat deforming spinal conditions for example, often require immobilizing or fusing vertebrae together by installing surgical implants to the affected bone structures. The implantation of pedicle screw fixation systems to correct and stabilize congenital and acquired deformities, trauma and degenerative diseases of the spine is well known. Such implants often include, for example, various screws or hooks fixed to vertebrae and linked by rods, plates or wires. Many different vertebra mounted spinal implants are known, however most share a common requirement for fixation of an element to a vertebral body: screw insertion. The use of screws, installed into the pedicle region of each vertebra requiring immobilization, remains a critical mainstay of spinal corrective surgery, but one fraught with a potential for error that, even given today's surgical devices and procedures, remains significant.

Traditional spinal surgical operations are highly invasive, often requiring large incisions which, while necessary to achieve sufficient spinal exposure, result in significant patient trauma and post operative pain. Computer assisted image guided surgical instrument navigation and percutaneous implant fixation are increasingly being used wherever possible in an effort to reduce the invasiveness of spinal surgery.

It is well known to use vertebral clamps having opposing jaws with teeth thereon for driving together and penetrating tissue and bone such that the clamp can be fixedly fastened to a spinous process of a vertebral body. Such clamps are typically quite long, about 20 cm in length, although smaller clamps intended to significantly limit the invasiveness of spine surgery, have more recently also emerged. The use of these clamps with an image guided surgery system, wherein the clamp comprises a trackable element thereon which can identify the position and orientation of the clamp, and therefore also that of the bone element to which it is fixed, is also well known.

Computer Assisted Surgery (CAS) systems have considerably enabled much more precise and accurately repeatable pedicle screw insertion during spinal surgical operations. However, surgical navigation in the spine, where multiple vertebral bodies can move relative to each other, as a result of patient breathing or other body movement for example, creates navigation difficulties unique to spinal surgery in general, and to pedicle screw placement and insertion in particular. It has been recently taught, for example by Bucholz et al. in U.S. Pat. No. 6,236,875, to modify and reposition the pre-operatively acquired anatomical image data set to match the actual position of the anatomical elements during the surgery. A single tracked clamp is fixed to a first vertebra into which a pedicle screw is to be placed, for example. Once the vertebra is registered with the computer model of itself, the trackable clamp fastened thereto permits tracking this registered vertebra only using the CAS system. Once work on the registered vertebra is completed, the entire clamp assembly is removed, and reinstalled on a second vertebra, which once registered, can then be tracked by the system. Therefore, in order to insert pedicle screws into a plurality of vertebrae, these steps must be repeated for each vertebra sequentially, and therefore only one vertebra is ever accurately tracked and therefore precisely located in space by the CAS system, at any one time. While only limited displacement between vertebrae naturally occurs, even the slightest movement of the patient during surgery, for example movement resulting from breathing, can cause enough relative displacement of the other vertebrae with respect to the one being tracked to cause their inaccurate depiction. Therefore the precise position and movement of the entire section of interest of the spine cannot be accurately located with only a single vertebra being tracked. Using individual tracking elements for each rigid body in spine surgery, while permitting intra-operative detection of each anatomical element, is impractical as having detectable members fixed to each vertebra takes up considerable space within the surgical field, limiting the workspace available to the surgeon, and often additionally resulting in a higher level of invasiveness. This is, however, what has been done to date.

In U.S. Pat. No. 6,226,548 Foley et al. disclose a CAS navigated apparatus which provides the ability to track a surgical instrument and implants such that percutaneous surgical operation can be performed on anatomical elements, such as vertebrae, which can intra-operatively move relative to each other. Foley et al. use a percutaneous bone clamp, which is fastened to a spinous process of a vertebra, and onto which is removably engaged a superstructure having a reference member including emitters for providing a positive indication of movement of the structure, and hence the vertebra to which it is fastened, to the surgical navigation system. The system can thereby positively indicate to the surgeon a change in position of the vertebrae from that identified in the pre-stored image scan, and provides a method to realign those body parts to correspond with a previously stored image or the image to correspond with the actual current position of the body parts.

However, if each rigid body is not individually detectable, any movement of the anatomical structures relative to one another during surgery can cause the pre-operatively scanned images to misrepresent the intra-operative anatomy, a possibility that could eventuate in very grave consequences. When a single vertebra is being tracked, only the spatial position and orientation of the lone tracked vertebral body can be accurately determined.

Additionally, when the spinal column in particular is the multiple-bone anatomical structure of interest, there exists difficulty in tracking all of its constituents. While spinal column bone clamps adapted to be fastened onto vertebra are known, whether tracked or not, it generally remains difficult to track the sacrum with these standard vertebral clamps currently in use. As the sacrum generally has very little process portion which protrudes, the sacrum provides no convenient clamping point permitting simple engagement of a tracked bone reference clamp. Without using a bone reference which requires fastening to the sacrum body using bone screws for example, it is currently difficult to use standard vertebrae reference clamps in order to identify and track the sacrum with an image guided surgery system.

Therefore, there nevertheless remains a need to provide a simple method of tracking a multi-bone moveable structure, such as the spinal column, and registering it with an anatomical image or model, such that the location of the multiple-bone moveable structure can be accurately determined intra-operatively by an image guided surgical system, without requiring displacement of the bone reference apparatus from one bone to another. There also remains a need to provide a vertebral clamp capable of conveniently engaging the sacrum, in order to permit tracking of the sacrum.

SUMMARY OF THE INVENTION

Accordingly, an object of the present invention is to provide a method for, and an apparatus permitting, the accurate tracking of a multi-bone moveable structure using a single reference tracker adapted for communication with an image guided surgical system.

It is another object of the present invention to provide a tracked multi-vertebral CAS reference clamp.

It is another object of the present invention to provide a vertebral clamp capable of providing variably selective compression and extension of vertebral bodies engaged therewith.

It is another object of the present invention to provide a surgical tool capable of simplifying, improving the precision, or improving speed of spinal implant surgery.

It is another object of the present invention to provide a CAS multi-vertebral reference clamp capable of simplifying the use of fluoroscopy for surgical navigation.

It is yet another object of the present invention to provide an apparatus capable of tracking the sacrum.

Therefore there is provided, in accordance with the present invention, a surgical device adapted for use with an image guided surgical system to facilitate monitoring inter-dependently mobile bone elements, comprising: a rigidly connected multiple-point anchor assembly releasably engageable to at least two inter-dependently mobile bone elements, immobilizing the bone elements such that no relative movement therebetween is possible, and thereby forming a complex rigid body comprising the immobilized bone elements and the multiple-point anchor assembly; and a trackable member, fastened to the multiple-point anchor assembly and comprising a detectable element adapted to be located and tracked in three dimensional space by the image guided surgical system, thereby defining position and movement of the complex rigid body.

In accordance with the present invention, there is additionally provided a method for monitoring position and movement of vertebrae using an image guided surgical system, comprising the steps of: attaching a rigidly connected multiple-point anchor assembly to at least two vertebrae located within a frame of reference of the image guided surgical system, thereby immobilizing the vertebrae relative to one another, the multiple-point anchor assembly being trackable and adapted to be located in three dimensional space by the image guided surgical system; and performing a registration of the at least two immobilized vertebrae, the immobilized vertebrae being tracked together permitting at least one of facilitated and improved registration.

In accordance with the present invention, there is also provided a use of a multiple-bone clamp with a common tracker in image guided surgery, comprising: attaching the rigidly connected multiple-bone clamp having a common tracker member to at least two inter-dependently mobile bone elements located within a frame of reference of an image guided surgery system, thereby immobilizing the vertebrae relative to one another; and tracking the multiple-point anchor assembly with the image guided surgery system such that the multiple-point anchor assembly is continuously located in three dimensional space.

BRIEF DESCRIPTION OF THE DRAWINGS

These and other features, aspects and advantages of the present invention will become better understood with regard to the following description and accompanying drawings wherein.

DETAILED DESCRIPTION OF THE PREFERRED EMBODIMENT

Figure 1:
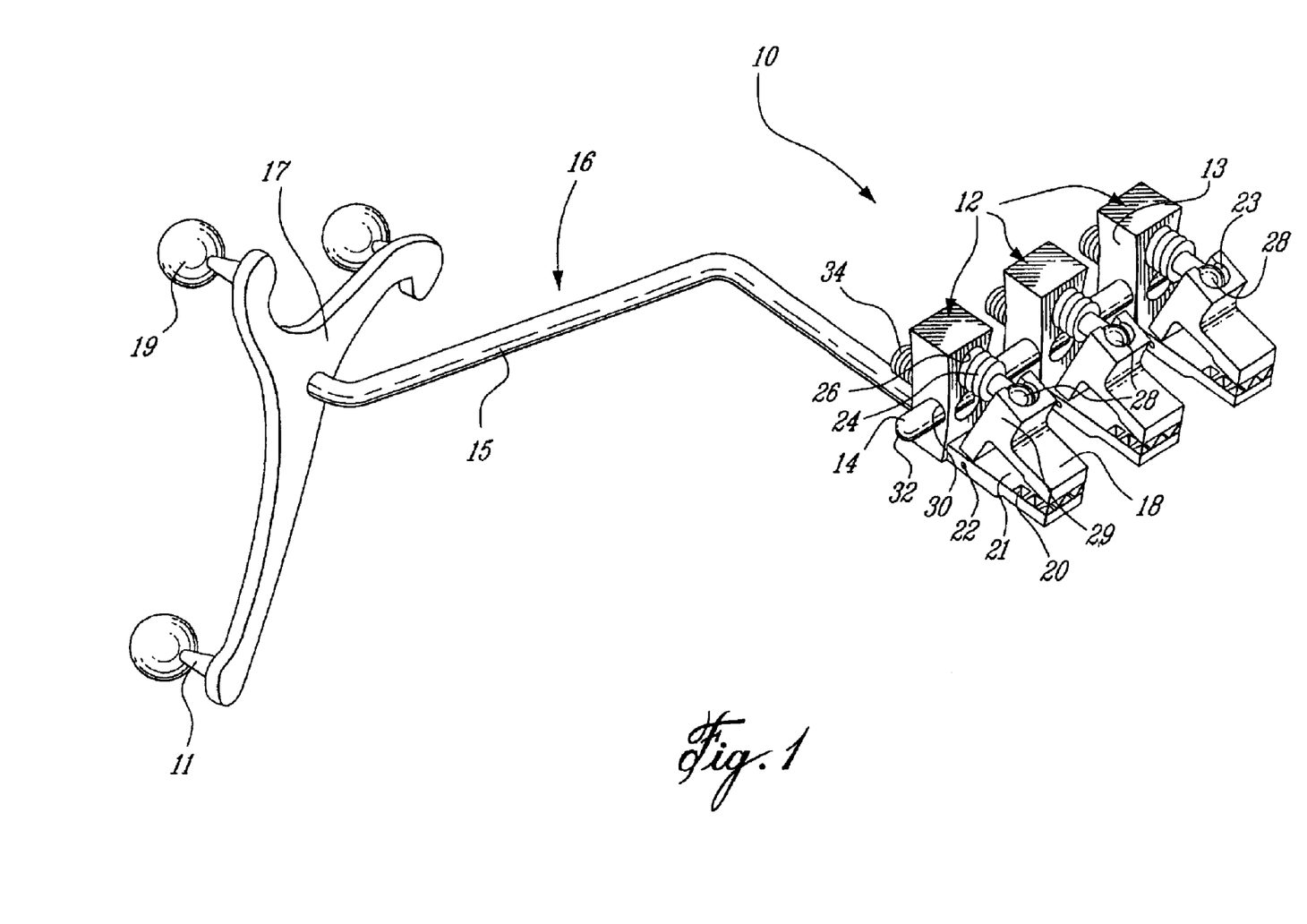
FIG. 1 is a perspective view of the CAS system trackable multi-vertebrae clamp according to the present invention.

Referring to FIG. 1, a surgical bone reference multiple-clamp assembly 10 preferably adapted for use with a CAS system capable of tracking the device. The multiple-clamp assembly 10 generally comprises at least two anchoring members 12 adapted for removably fixation to bones of the patient. The multiple-clamp assembly is preferably for use with vertebrae of the spinal column, such that several vertebrae can be clamped together, restraining all relative movement therebetween, and subsequently tracked as a single body. This permits accurate determination of the position and orientation of several normally articulated bone structures of a linkage without requiring a plurality of trackable members which would clutter the surgical field. When used as a reference clamp for vertebrae, the present multiple-clamp assembly preferably comprises three anchoring clamps 12, adjustably fastened together with a linking bar 14 to form a rigidly connected triple clamp. The trackable member 16 is fastened, preferably permanently although a disengageable connection could be used to permit disengagement if required, to one of the anchoring clamp members 12.

Although the present multiple-anchor bone reference assembly will be generally described and depicted as a tracked multiple-vertebrae clamp, it is to be understood that the present bone reference can equivalently be fastened to any two, at least, moveable bone elements such that they can be clamped together and therefore relatively immobilized, and tracked as a unit by a CAS system. The present multiple-anchor assembly permits at least two bone elements to be clamped together, whether discrete bones that normally permit relative movement therebetween or two portions of the same bone which are normally relatively fixed but have been abnormally separated and must be fastened together for a specific surgical procedure. For example, in an alternate embodiment, the present multiple-anchor bone reference assembly can be used for fracture fixation. In this case, at least one anchoring clamp is fastened to the bone on either side of the fracture point, and the anchoring clamps 12 are fastened together with the linking bar 14, such that the two portions of the fractured bone are immobilized relative to one another, and can then be located and tracked by a CAS system. The use of a fluoroscope to acquire the anatomical images would therefore permit the multiple-anchor bone reference assembly to be very useful for fracture fixation surgery in trauma cases, where the fluoroscope x-ray shots can be taken intra-operatively. Additionally, while preferably adapted for use with a CAS system, the present bone clamp could be equivalently used without the trackable member for use as a simple multiple bone clamp which fastens several inter-dependently mobile bone structures together.

Each clamp member 12 comprises a pair of jaws, namely a pivoting jaw 18 and a fixed jaw 21, adapted to be closed together to anchor the clamp member onto a vertebral spinous process. Both jaws comprise sharp, inwardly projecting spikes or teeth 20, permitting penetration of both soft tissue and bone, which facilitate secure engagement on the vertebrae. The teeth 20 are preferably machined from the jaws, enabling the teeth to be located closer to the proximal end of the jaws, thereby permitting a better grip on the vertebral spinous process. The moveable jaw 18 pivots about pin 22 at the distal end of the fixed jaw 21. Other jaw clamping mechanisms could also be used, for example both jaws could move, or the jaws could close while remaining parallel to one another. The pivoting jaw 18 is actuated by a bi-directional clamping screw 24, which acts to open or close the jaws of the clamp. The clamping screw 24 extends through a threaded hole 26 the body portion 13 of the clamp members and is rotationally driven by a hex head at the distal end of the screw. The clamping screw 24 preferably has a spherical tip 28 which extends from a narrowed stem section of the screw following the end of the threads at the proximal end of the clamping screw. The narrow stem section is adapted for extending through slot 23 in the top of the lever portion 29, outwardly extending from the pivot point 22, of the pivoting jaw 18 such that the special screw tip 28 is received within the cylindrical shaped socket 25 of the pivoting jaw 18. This clamping mechanism enables the ball tip 28 of the clamping screw 24 to either push or pull, with equal effectiveness, on the lever portion 29 of the pivoting jaw 18, causing the jaws to efficiently close or open, respectively. The clamp members are relatively small and compact in comparison with many bone clamps of the prior art, enabling the invasiveness of the surgery to be considerably reduced if required, as smaller incisions are possible.

As mentioned above, the clamp members 12 are adjustably fastened together with a linking bar 14. Each body portion 13 of the clamp members comprises a slot 30 formed therethrough, corresponding to the cross-sectional shape of the linking bar used. The linking bar preferably has a full-length flattened face 32, creating a D-shaped cross-sectional area of the linking bar 14. Each clamp member 12 is fastened to linking bar 14 by a locking screw 34, which is threaded through the body portion 13 of the clamp member and frictionally engages the flattened face 32 of the linking bar 14, thereby securing the clamp member in place thereon. While different linking bars could similarly be employed, the D-shaped bar and slot provide several advantages over a linking rod and bore having circular cross-sections, for example. The non-circular cross-section eliminates any possibility of the clamp members 12 rotating about the linking bar. The flattened face 32 of the D-shaped linking bar also provides for a better contact surface for the locking screw 34 to engage the bar. Using a D-shaped linking bar 14 with circular cross-sectioned slots 30 in the clamp members 12 is equally envisioned, and preferable if some relative rotation of the clamp members 12 with respect to one another is desired in order to permit the clamps to best engage the vertebrae to which they are respectively engaged.

The trackable member 16 generally comprises a support rod 15 for mounting a detectable tracker head element 17, which includes detectable element mounting posts 11 for receiving detectable markers 19 thereon, to the multi-clamp assembly previously described and comprising the clamp members 12 releasably fastened together with linking rod 14. To each mounting post 11 is removably fixed an optically detectable sphere 19. The detectable spheres are coated with a retro-reflective layer in order to be detected by, for example, an infrared sensor using axial illumination. Cameras of the CAS system can therefore detect the position of each optically detectable sphere 19 illuminated by infrared light. Each detectable marker element 19 can equally be any other type of position indicator such as a light emitting, diode or detectable electromagnetic indicator, provided each can be detected by the type of sensor used by the CAS system. The CAS surgical instruments used, such as for example a probe, can be of a variety of different types, providing they can be detected by the type of CAS system used. Along with the optical and electromagnetic systems mentioned above, other types of CAS systems can alternately be used, such as for example those which use ultra-sound or laser as a means for position identifying.

The CAS multiple-vertebrae clamp of the present invention is preferably intended to be used in conjunction with an optical tracking system which uses a network of cameras to locate the trackable member 16, or more specifically to locate the identification markers 19 of the detectable element 17, so that their position and movement can be tracked during the surgery. Either pre-operative computed tomography (CT) scans or intra-operative fluoroscopic images of the patient are used to create an anatomical model or image which is displayed on monitors during surgery and provides the surgeon with an accurate representation of the specific body parts or targeted elements of the patient. The anatomical models or images can also be acquired and/or generated using fluoroscopy, magnetic resonance imaging, ultrasound and/or landmark digitization techniques. The multi-point anchoring bone reference clamp of the present invention is then fixed to the desired patient bone structures, such that the anatomical position and orientation of the bones can be registered to the appropriate virtual bone models of the patient, or the position and orientation in 3D space of the anatomical images can be mathematically related to the reference clamp. This therefore matches the patient anatomy with the anatomical image displayed on the monitor, such that the position of the bone structures, to which the present multi-point anchoring clamp is fixed, can be shown graphically.

Figure 2:
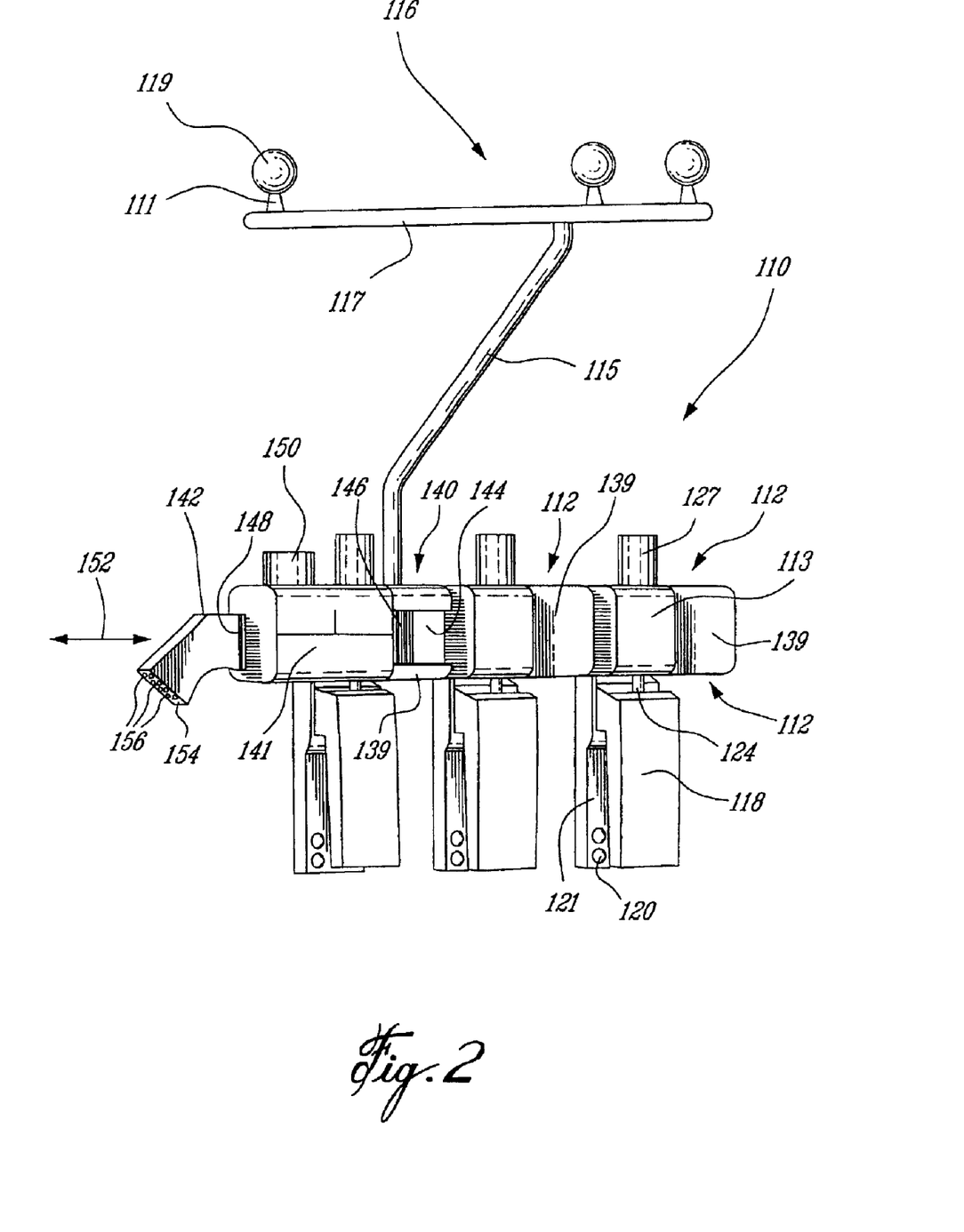
FIG. 2 is a perspective view of an alternate trackable multiple-vertebrae clamp according to the present invention having a sacrum engaging extendable press member.
Figure 3:
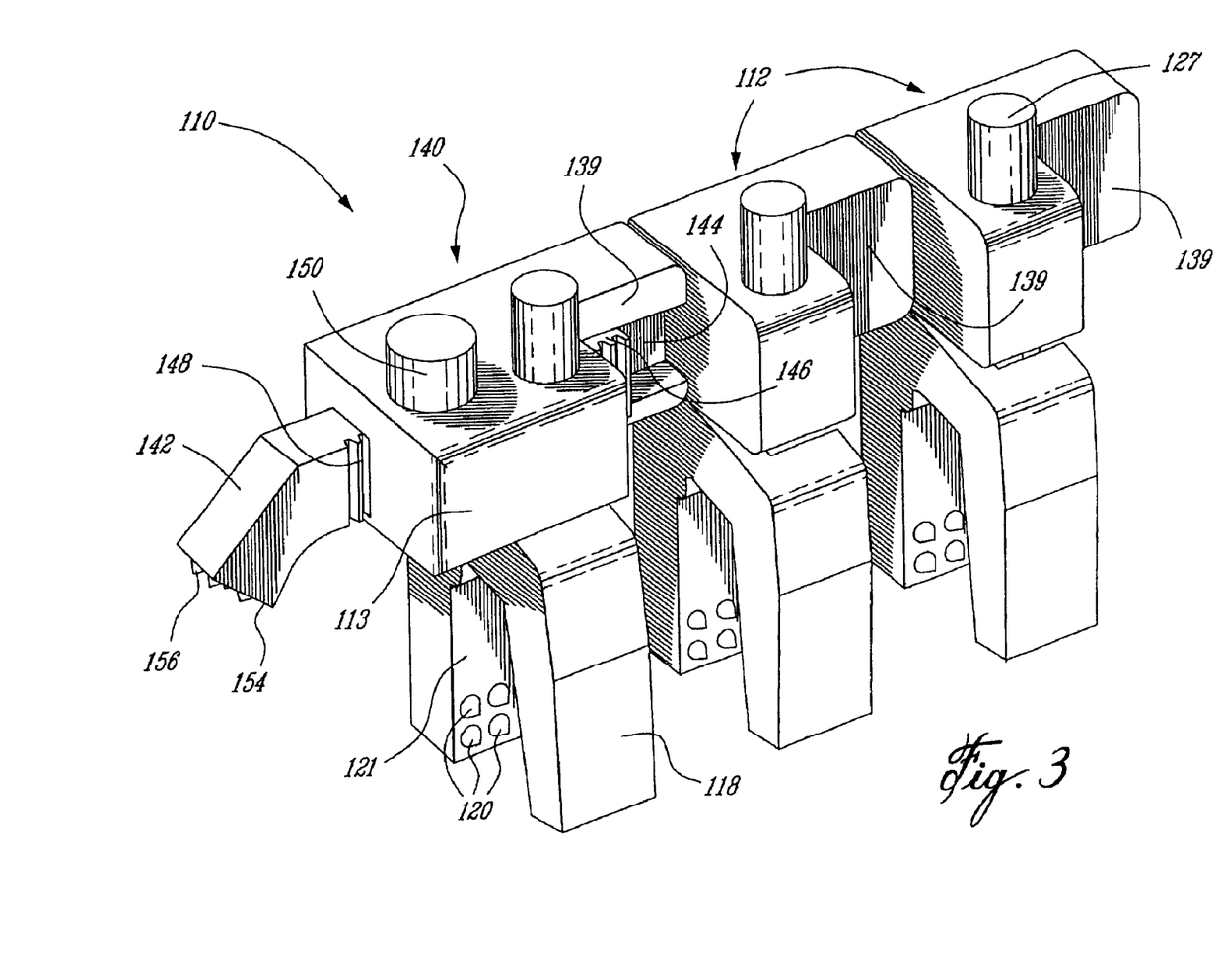
FIG. 3 is an enlarged perspective of a multiple-vertebrae non-tracked bone clamp with a sacrum engaging extendable press member.

Referring now to the alternative embodiment of the present invention shown in FIG. 2 and FIG. 3, the multi-anchor assembly 110 comprises two different anchoring members, namely standard clamping anchoring members 112, and a multi-acting anchoring member 140. The clamping members 112 operate similarly to the clamp members 12 described above. Pivoting jaw 118 and fixed jaw 121, having inwardly directed tissue engaging teeth 120, close to attach the clamping members 112 the vertebrae spinous processes, when the present instrument is used for spinal surgical applications for example. Clamping screw 124, extending through the body portion 113 of the clamping member 112 and being driven by hex head 127, manually actuates the jaws to open and close them as required.

Each anchoring member of the multi-anchor assembly 110 comprises a linking body portion 139, preferably integrally formed with the main body portion 113 of the anchoring members. This linking body portion 139 acts to interconnect each anchoring member making up the rigidly connected multi-anchor assembly with the adjacent anchoring member. The actual connection used to fasten one to another can be any disengageable mechanical linkage capable of rigidly fastening one anchor member with the next. While the multi-anchor assembly 110 is depicted with the integrally formed anchor member linking body portions 139, using a discrete linking bar to interconnect the anchoring members 112/140, such as that shown in FIG. 1, can equivalently be used.

The multi-acting anchoring member 140 provides two distinct anchoring methods to immobilize the bone elements of the articulated bone linkage to which the present invention is attachable. While generally depicted and described herein as being multi-acting, namely as having both a clamp portion similar to the clamping members 112 and an extending press 142, the anchoring member 140 can also comprise just one of the two anchoring methods. The press member 142 is preferably used to engage the sacrum, when the multi-anchor assembly 110 is used as a CAS bone reference on the vertebral column. The sacrum is often difficult to immobilize relative to the other vertebrae, as there is usually little or no spinous process protruding therefrom, and consequently no convenient attachment point for standard clamp-type anchors. The anchoring member 140 provides the ability to be attached to a vertebra using the jaws 118 and 120 of the clamp portion which move relatively together in a direction substantially perpendicular to a longitudinal axis of the spine, while the sacrum press member 142 can be extended from the slot 144 in the main body portion 141 of the anchoring member 140 in a direction substantially parallel to the longitudinal axis of the spine. The press member 142 comprises an elongated rack portion 146, having gear teeth 148 thereon, which is received within the slot 144 and is engaged with, and driven by, the rotatable pinion gear 150. Rotation of the pinion gear 150 therefore extends or retracts the sacrum press member 142 in a direction indicated by arrow 152 in FIG. 2. The press member 142 is preferably formed having an angled proximal end portion, to better engage the sacrum and to limit somewhat the travel distance required for the press face 154 to contact the sacrum. Teeth 156 are located on the press face 154 to ensure good engagement with the bone surface.

The surgical multi-anchor assembly 110 as shown in FIG. 2 comprises a CAS trackable member 116 fastened thereto, comprising a detectable element 117 having position identification markers 119 and supported by support rod 115, which permit position and orientation determination of the device using an image guided surgical system as described above. In this case, the multi-anchor assembly 110 is used as principally intended, as a CAS trackable multi-bone reference clamp. However, the multi-anchor assembly 110 could also be used without the CAS trackable member 116, such as shown in FIG. 3, as a simple multiple-bone fastening clamp. Such a device could be used for any surgical application requiring several individually mobile bone elements of an interrelated articulated bone linkage to be fastened together and immobilized.

Figure 4:
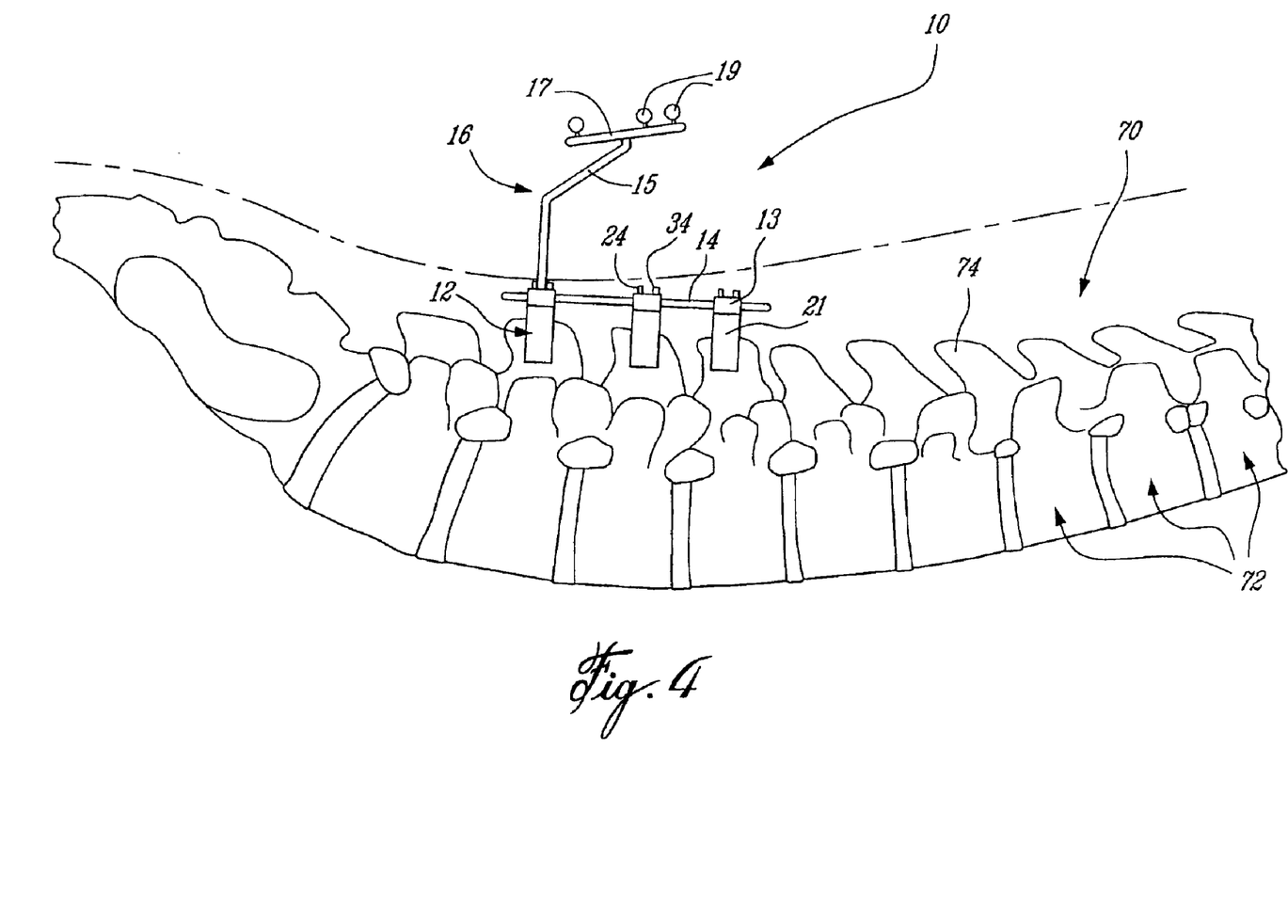
FIG. 4 is a side elevation view of the first embodiment of the trackable multi-vertebral clamp of FIG. 1 installed on a spinal column.

In FIG. 4, the multi-vertebrae CAS reference clamp assembly 10 is depicted in a sample installation setup, fastened to spinous processes 74 of the vertebrae 72 of a spinal column 70. The installation method of the assembly would preferably be as follows: ensure that the clamp members 12 are loosely placed onto the linking bar 14 but are not fully tightened thereto; individually install each clamp member 12 to a vertebra to be tracked by turning the clamping screws 24 to close the jaws 18 and 21 of the clamp about a spinous process of the vertebra, such that the clamps retain the clamp members in place but are not fully tightened; ensure that the location of the detectable element 17 of the trackable member 16 is such that the CAS system can locate and uniquely identify the trackable member; finish tightening each clamping screw such that clamp members 12 are rigidly fastened to the respective vertebrae; adjust the spinal column into the desired position, preferably such that the linked clamp assembly exerts a compressive force on adjacent spinous processes, forcing them away from one another and thereby best eliminating relative movement therebetween; and then securely tighten the locking screws 34 to fix the clamp members 12 in position on the linking bar 14, thereby immobilizing the clamped vertebrae which can then be tracked together.

Figure 5:
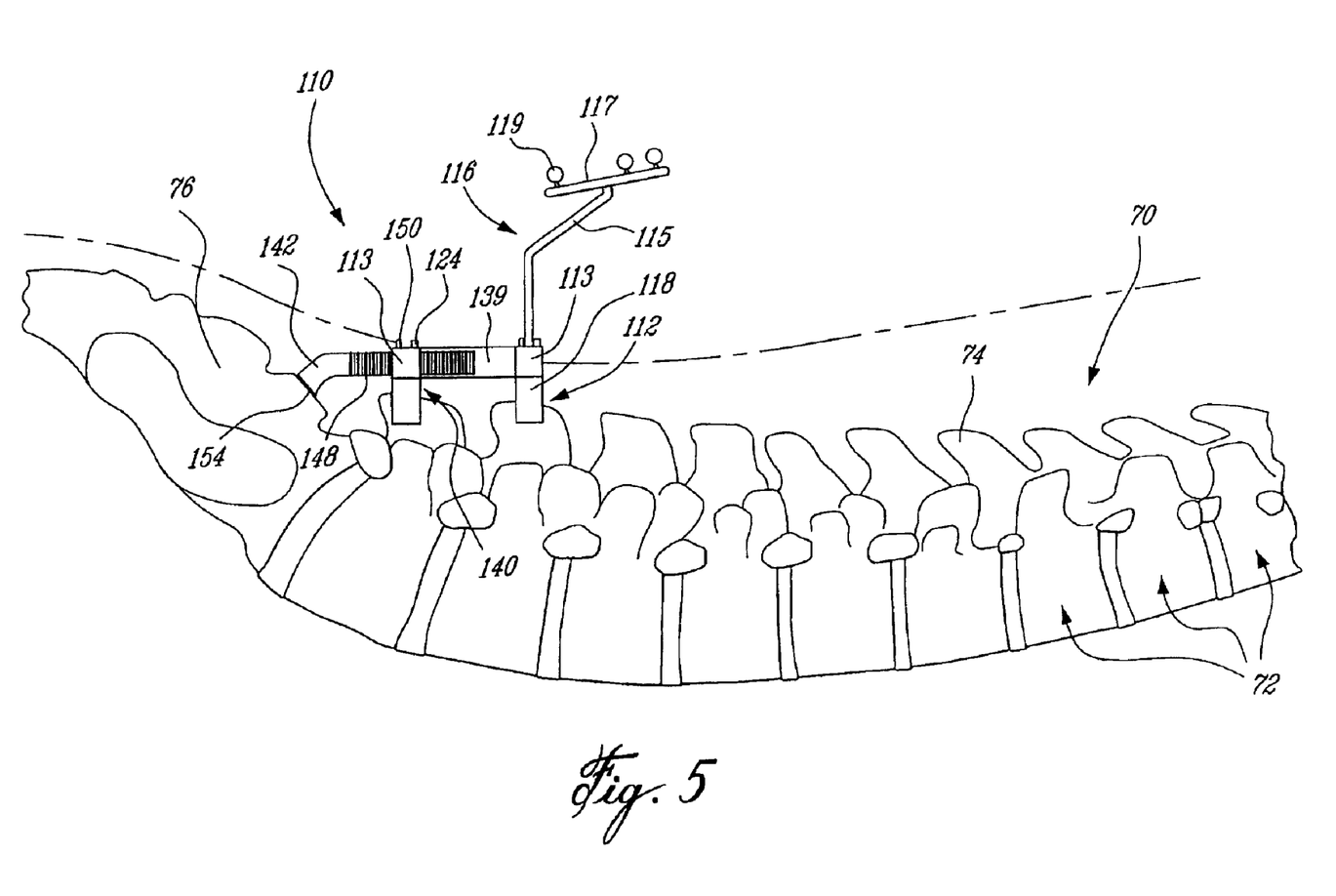
FIG. 5 is a side elevation view of the alternate embodiment of the trackable multi-vertebral clamp of FIG. 2 installed on a spinal column.

FIG. 5 shows a similar set-up of the alternate multiple-point anchor assembly 110, installed on a spinal column 70. The preferred installation process is similar to that described above. However, as the adjacent anchoring members are preferably already engaged together, the spine and the entire assembly should be adjusted in place to ensure exact location and spinal curvature is achieved before the clamping screws 124 are finally tightened. Although the clamping members 112 are generally directly engaged together, longitudinal adjustment such as that permitted by the linking bar of the multiple-clamp assembly 10 is nevertheless possible. Once the jaws of the clamping members 112 are fastened in the correct location to the spinous processes 74, the sacrum press member 142 can be extended towards the sacrum 76 by rotating the pinion gear 150. Once the press face 154 engages the surface of the sacrum 76, limited further rotation of the pinion gear will put pressure on the sacrum, causing it to pivot until immobilized relative to the clamped vertebrae. In both the multi-vertebrae reference clamp assembly 10 and the alternate multi-anchor assembly 110, torsional rotation between the clamped vertebrae is prevented, as the linking bar 14 and the linking body portion 139 preclude relative rotation of the adjacent clamp/anchoring members, and therefore accordingly also prevent relative torsional rotation of the respective clamped vertebrae.

The location of the trackable elements 16 and 116 relative to the base linked multi-clamp assembly as depicted in all figures is intended to be representative only. The trackable members should be fastened to the multi-clamp assembly as assembled such that it does not obstruct the operating field for the surgeon and does not impede clear access to the vertebrae to which the clamps are engaged, while remaining in unobstructed line of sight with the cameras of the image guided surgical system. The cameras are to be moved as necessary to best ensure this. Similarly, the clamps engaged to the spinous processes of the immobilized vertebrae are installed thereto, and relative to one another, such that clear access to the pedicles of the immobilized vertebra remains ensured.

With the complete assembly installed, no reasonable force applied on the vertebrae during surgery will create relative displacement between them in any direction. Therefore, with the tracker member rigidly connected to the reference clamp assembly and once sufficient registration of the immobilized vertebrae is achieved, the displacement matrix determined by the CAS system for any detected movement of the tracker can be similarly applied to all vertebrae clamped together, permitting accurate representation on the CAS system of the location of the vertebrae.

Once the vertebrae are securely clamped together, they must be registered with the corresponding anatomical images thereof. These can be obtained either from pre-operative CT scans which are used to create the 3D virtual models of the spinal column, or from 2-D fluoroscopic images taken intra-operatively. With single-vertebra CAS reference clamps of the prior art, a full registration of each vertebra had to be performed. If more than one vertebra was to be operated on, a full registration of a first vertebra to which the clamp was affixed had to be performed, and once the work was completed, the clamp was moved to a second vertebra and a second full registration of the second vertebra was necessary, and so on. The present invention permits using a reduced number of registration steps and permits all of the registration points to be acquired at the same time, thereby simplifying the time required for accurate registration of several vertebrae. Additionally, if fluoroscopy is used, the present multi-vertebrae clamp significantly reduces the number of x-rays required to be taken with the C-arm, and therefore reduces the amount of radiation to which those in the operating room are exposed and also saves the considerable time required to take each x-ray shot. When the term registration is used herein, it is intended to include both acquiring a number of points on the surface of the bone structures, and matching the points to a surface of a 3D computer model of the bone structures generated from a pre-operatively taken CT scan, and the calibration of intra-operatively taken fluoroscopic images of the bone structures such that their positions in space are accurately depicted relative to the surgical instruments and the patient reference.

When CT-based images are being used, once the multiple-point anchoring clamp assembly is securely engaged to the vertebrae thereby immobilizing them relative to the location of the trackable member, a first vertebra is registered to the computer model element thereof by acquiring a plurality of points, either pre-determined and sequentially identified by the CAS to the surgeon or randomly selected by the surgeon, on the surface of the vertebrae using a calibrated CAS probe. The points on the physical vertebra are then matched with corresponding points on the 3D model, thereby registering the CAS system bone model to the tracked position in space of the anatomical counterpart. Once this full registration process is completed for a first clamped vertebra, limited registrations can be performed on the other vertebrae immobilized relative to the first fully registered vertebra. These simplified registrations of the further vertebrae in the multiple-point clamp assembly can comprise only the acquisition of a minimal number of points on the surface of the further vertebrae. This significantly reduces the number of acquisition points required to be able to accurately register all but the first vertebra registered. This reduces the time required for accurate registration of several vertebrae, and as once the registration is complete the position of several vertebrae is available, considerable time savings and surgical operational simplification are achieved.

When fluoroscopic anatomical images are being used, the registration process required is slightly different, however the advantages that the multiple-vertebra clamp provides remain considerable. Using intra-operatively acquired fluoroscopy images is particularly useful for trauma cases and in situations where the optimal accuracy provided by the more radiation intensive CT scans is not required. When traditional patient reference bone clamps are used, after each vertebra is operated on, the reference clamp had to be moved to the next vertebra and another fluoroscopic x-ray had to be taken. An intra-operatively taken fluoroscopic image therefore has to be taken for each tracked bone structure. Once the present multi-vertebrae clamp is installed, only one x-ray has to be taken to precisely locate all of the immobilized vertebra visible in the image. This significantly reduces the number of x-ray shots required, thereby reducing overall radiation exposure to those in the OR, and saving the considerable time that is required to set up and take every fluoroscopic image. Therefore, the advantages of using the present tracked multi-vertebrae clamp are considerable when used in conjunction with fluoroscopy based CAS.

In an alternate embodiment, a variant structure is used to similarly immobilize the vertebrae that are to be tracked, in order to permit accurate pedicle screw insertion for example. By using selectively expanding devices disposed substantially longitudinally between adjacent vertebral spinous processes, rather than clamped directly thereto as in the preferred embodiment describe above, a compressive force therebetween can be applied. This forces the compressed vertebrae apart, thereby eliminating any relative movement between the engaged vertebrae in a substantially vertical plane extending through the longitudinal axis of the spinal column. To eliminate the possibility of torsional rotation between engaged vertebrae, additional stringer elements are provided that preferably extend longitudinally along either side of the vertebrae and can be transversely clamped together, engaging the sides of the vertebral spinous processes and thereby preventing any relative torsional rotation therebetween. Alternately, these stringer elements are eliminated and alternate expanding devices are used which wrap further around both sides of each spinous process sufficiently to prevent any relative torsional rotational therebetween.

The embodiments of the invention described above are intended to be exemplary only. The scope of the invention is therefore intended to be limited solely by the scope of the appended claims.

What is claimed is:

1. A surgical device adapted for use with computer assisted surgical system to facilitate monitoring inter-dependently mobile bone elements, comprising:
    a rigidly connected multiple-point anchor assembly releasably engageable to at least two inter-dependently mobile bone elements, immobilizing the bone elements such that no relative movement therebetween is possible, and thereby forming a complex rigid body comprising the immobilized bone elements and the multiple-point anchor assembly; and
    a trackable member, fastened to the multiple-point anchor assembly and comprising a detectable element adapted to be located and tracked in three dimensional space by the computer assisted surgical system, thereby defining position and movement of the complex rigid body.

2. The device as defined in claim 1, wherein the multiple-point anchor assembly provides one of a compressive and a tensile force between the immobilized bone elements engaged therewith.

3. The device as defined in claim 1, wherein the multiple-point anchor assembly comprises at least two discrete anchoring members.

4. The device as defined in claim 3, wherein the anchoring members are inter-fastenable and adjustable substantially longitudinally relative to the bone elements.

5. The device as defined in claim 3, wherein at least one of the anchoring members comprises a clamp adapted for fixation to one of the bone elements.

6. The device as defined in claim 5, wherein the clamp comprises opposing jaws operable to close together for releasable attachment with the bone element.

7. The device as defined in claim 4, wherein the anchoring members, having bores therethrough and being arranged such that the bores substantially correspond, are inter-fastened by a linking bar extending through the bores to which each anchoring member is fastenable.

8. The device as defined in claim 7, wherein the linking bar has a pre-determined shape adapted to conform to the shape of a longitudinal axis of the bone elements.

9. The device as defined in claim 1, wherein the bone elements comprise vertebrae.

10. The device as defined in claim 9, wherein the vertebrae include spinous processes, and the discrete anchoring members are engageable thereto such that pedicles of the vertebrae remain accessible.

11. The device as defined in claim 3, wherein at least one of the anchoring members comprises a sacrum press member.

12. The device as defined in claim 11, wherein the sacrum press member is longitudinally extendable relative to the spinal column.

13. The device as defined in claim 12, wherein the extending sacrum press member comprises a pinion gear driven rack providing substantially rectilinear displacement thereof.

14. The device as defined in claim 9, wherein the anchoring members comprise three vertebral clamps, each adapted for clamping to a vertebra and being inter-fastened such that the three vertebrae are rigidly clamped together, and thereby trackable as a single unit by the computer assisted surgical system.

15. A method for monitoring position and movement of inter-dependently mobile bone elements using an computer assisted surgical system, comprising the steps of:
providing a surgical device having a rigidly connected multiple-point anchor assembly releasably engageable to at least two bone elements and a trackable member fastened to the multiple-point anchor assembly, the trackable member including a detectable element which is locatable and trackable in three dimensional space by the image guide surgical system; and
attaching the rigidly connected multiple-point anchor assembly to at least two bone elements located within a frame of reference of the image guided surgical system, thereby immobilizing the bone elements relative to one another such that no relative movement therebetween is possible and forming a complex rigid body including the immobilized bone elements and the multiple-point anchor assembly which is trackable by the image guided surgical system.

16. The method as defined in claim 15, further comprising performing a registration of the at least two immobilized bone elements, the immobilized bone elements being tracked together using the multiple-point anchor assembly permitting at least one of facilitated and improved registration, and tracking position and movement of the complex rigid body using the computer assisted surgical system.

17. The method as defined in claim 16, wherein the bone elements are immobilized in a predetermined position in accordance with a predetermined constraint among the bone elements, and the registration is performed having regards to the predetermined constraint to permit at least one of facilitated and improved registration.

18. The method as defined in claim 17, wherein registration is performed by acquiring a number of points on the surface of a first bone element, and matching the points to a surface of a 3D computer model of the first bone element generated from a pre-operatively taken CT scan.

19. The method as defined in claim 18, wherein limited registrations, requiring a reduced number of points to be acquired on the surface of each bone element, are performed on each further bone element, thereby reducing registration time.

20. The method as defined in claim 18, wherein full registrations are performed on each further bone element and the registration accuracy is improved.

21. The method as defined in claim 18, wherein a probe is provided to acquire the registration points.

22. The method as defined in any one of claims 15 to 20, wherein the registration is performed for each immobilized bone element, and a 3D model of each bone element is displayed one at a time during surgery.

23. The method as defined in claim 15, wherein registration is performed by matching reference artifacts from an intra-operatively taken fluoroscopic image of the bone elements to the location of the reference artifacts at the time the fluoroscopic image was taken, the position and orientation of the reference artifacts being determined by the computer assisted surgical system.

24. The method as defined in claim 23, wherein a reduced number of fluoroscopic images of the bone elements are required, as all of the immobilized bone elements can be located with a single fluoroscopic image.

25. The method as defined in claim 15, wherein the bone elements comprise vertebrae and the step of attaching the multiple-point anchor assembly further comprises engaging the multiple-point anchor assembly to a posterior side of the two vertebrae such that posterior surfaces of pedicles of the two vertebrae remain accessible.

26. The method as defined in claim 25, further comprising engaging the multiple-point anchor assembly to projecting spinous processes of the two vertebrae.

27. The method as defined in claim 15, wherein the multiple-point anchor assembly comprises at least one clamp releasably engageable to at least one of the two bone elements, the step of attaching the multiple-point anchor assembly further comprising clamping opposed jaws of the clamp onto a portion of the at least one bone element.

* * * * *